US00PP15652P2

(12) United States Plant Patent
Bradford

(10) Patent No.: US PP15,652 P2
(45) Date of Patent: Mar. 15, 2005

(54) INTERSPECIFIC TREE 'SWEETCOT'

(50) Latin Name: *Prunus salicina* and *Prunus armeniaca*
Varietal Denomination: Sweetcot

(76) Inventor: Lowell Glen Bradford, 12439 E. Savana Rd., Le Grand, CA (US) 95333

( * ) Notice: Subject to any disclaimer, the term of this patent is extended or adjusted under 35 U.S.C. 154(b) by 74 days.

(21) Appl. No.: 10/746,714

(22) Filed: Dec. 29, 2003

(51) Int. Cl.[7] ..... A01H 5/00
(52) U.S. Cl. ..... Plt./180
(58) Field of Search ..... Plt./180

*Primary Examiner*—Bruce R. Campell
*Assistant Examiner*—S. B. McCormick-Ewoldt

(57) ABSTRACT

The present interspecific variety is characterized by a medium size, vigorous, hardy, and productive tree that is self-unfruitful and can be pollinated by a late blooming apricot. The fruit matures under the ecological conditions description during the last week in June, with first picking on Jun. 22, 2003. The fruit if medium in size, dark purple in skin color with pubescence, clingstone in type, orange yellow in flesh color, very firm in texture, and very sweet in flavor. The variety was developed as a first generation cross using 'Angeleno' U.S. Plant Pat. No. 2,747) plum as the seed parent by an unknown pollen source containing some degree of apricot.

1 Drawing Sheet

Botanical classification: Interspecific between *Prunus salicina* and *Prunus armeniaca*.
Variety denomination: 'Sweetcot'.

BACKGROUND OF THE INVENTION

In a continuing effort to improve the quality of shipping fruits, I, the inventor, typically hybridize a large number of peach, nectarine, plum, apricot, and cherry seedlings each year. I also grow a lesser number of open pollinated seeds of each of these fruits. The present invention relates to a new and distinct variety of interspecific tree, which has been denominated varietally as 'Sweetcot'.

During the 1996 blooming season I isolated as entire 'Angeleno' (U.S. Plant Pat. No. 2,747) plum tree by covering it with a plastic covered house. I placed a hive of bees inside the house and brought various bouquets of plum, apricot and plum-apricot interspecific trees to hybridize the 'Angeleno' plum tree. Upon the completion of the bloom, the house and bees were removed and the resulting fruit was allowed to ripen. Upon maturity, the fruit was harvested and their seeds were germinated and grown as seedlings on their own root in my greenhouse. Upon reaching dormancy that fall, the seedlings were transplanted to a cultivated area of my experimental orchard near Le Grand, Calif. in Merced County (San Joaquin Valley). The group of seedlings were labeled "House 8". During the 2000 evaluation season, I selected the present variety as a single tree from the group of seedlings described above because the tree produced a heavy crop of firm fruit that was very sweet in flavor. The present variety exhibited several indications that it was itself an interspecific, such as pubescent skin, orange yellow flesh, and leaves resembling apricots. Subsequent to origination of the present interspecific tree, I asexually reproduced it by budding and grafting in the experimental orchard described above, and such reproduction of plant and fruit characteristics were true to the original plant in all respects. The reproduction of the variety included the use of 'Nemaguard' (unpatented) rootstock upon which the present variety was compatible and true to type.

The present variety is similar to its seed parent, 'Angeleno' (U.S. Plant Pat. No. 2,747), by being self-unfruitful and by producing fruit that is globose in shape, firm in texture, and dark purple to black in skin color, but is very distinguished therefrom by having apricot type leaves and blossoms and by producing fruit that has pubescent skin, that is orange yellow in flesh color, that is much sweeter in flavor, and that matures in late June rather than early September, or about seventy days earlier.

SUMMARY OF VARIETY

The present interspecific variety is characterized by a medium size, vigorous, hardy, and productive tree with apricot type leaves, blossoms, and skin pubescence. Being self-unfruitful, the present variety requires cross pollination from an apricot or plum that blooms during the late season. The present variety's abundance of blossoms and pollen entices strong bee activity to facilitate pollination. The fruit matures under the ecological conditions described during the last week in June, with first picking on Jun. 22, 2003. The fruit is medium in size, dark purple in skin color, clingstone in type, orange yellow in flesh color, very firm in texture, and very sweet in flavor.

DRAWING

The accompanying photograph exhibits four whole fruits positioned to display the characteristics of the skin color and form, one fruit divided transversely to the suture plane to reveal the flesh and stone, and typical leaves.

DETAILED BOTANICAL DESCRIPTION

Referring now more specifically to the pomological characteristics of this new and distinct variety of interspecific tree, the following has been observed under the ecological conditions prevailing near Le Grand, Merced County (San Joaquin Valley), Calif., and was developed at the state of firm ripe on Jun. 28, 2003, on the original tree during its seventh growing season. All major color code designations are by reference to the Inter-Society Color Council, National Bureau of Standards. Common color names are also used occasionally.

Tree

Size: Medium, reaching and maintaining a height of 11" [3.4 m.] and a spread of 7' [2.1 m.] after seven growing seasons utilizing typical dormant pruning.

Vigor: Medium, responding typically to irrigation and fertilization. The variety grows about 3' [0.9 m.] of surplus top-growth during the spring and summer. The plant should be grown on a standard commercial rootstock for production purposes.

Growth: Upright and dense.

Form: Vase formed.

Hardiness: Hardy with respect to central California winters.

Heat tolerance: Observed to perform adequately in typical central California climatic conditions, which typically include prolonged periods of heat.

Drought tolerance: Variety is developed for commercial orchards and requires regular irrigation.

Production: Productive.

Fertility: Self-unfruitful, requiring cross pollination by a suitable late seasonal blooming apricot or plum. The variety was pollinated by '17G415' (unpatented) apricot in 2003.

Bearing: Regular bearer.

Trunk:

*Size.*—Medium, reaching a maximum diameter of 3½" [89 mm.] after the seventh growing season.

*Texture.*—Very shaggy.

*Bark color.*—Dark grayish reddish brown [47. d.gy.rBr] over a Grayish brown [61. gy.Br] primary.

*Lenticels.*—Approximate mumber per square inch: 12. Color: Light orange yellow [70. l.OY]. Typical size: ⅛" to ⅜" [3.2–9.5 mm.].

Branches:

*Size.*—Diameter of limb is 1½" [38 mm.] measured 12" above the crotch, typical of *Prunus salicina* and *Prunus armeniaca,* and dependent upon cultural practices and climatic conditions.

*Texture.*—Rough to shaggy.

*Color.*—1st year wood topside: Grayish red [19. gy.R]. 1st year wood underside: Strong yellow green [117 s.YG]. Older wood: Dark yellowish brown [78 d.yBr].

*Lenticals.*—Approximate number per square inch: 24. Color: Light orange yellow [70. l.OY]. Typical size: 1/16" to ⅛" [1.6–3.2 mm.].

Leaves:

*Size.*—Medium. Average length: 2¾" [70 mm.]. Average width: 2 1/16" [52 mm.].

*Arrangement.*—Alternate.

*Thickness.*—Medium.

*Form.*—Oval.

*Apex.*—Aristate.

*Base.*—Rounded.

*Surface.*—Smooth.

*Color.*—Dorsal surface: Dark olive green [126. d.OlG]. Ventral surface: Moderate olive green [125. m.OlG].

*Margin.*—Finely serrate.

*Venation.*—Pinnately net veined.

*Petiole.*—Average length: 13/16" [20.6 mm.]. Average thickness: 3/64" [1.2 mm.]. Color: Moderate yellow green [120. m.YG].

*Stipules.*—Number: 2 per young leaf and 6 per growing point. Average length: ¼" [6.4 mm.]. Color: Brilliant yellow green [116. brill.YG] to Grayish red [19. gy.R] in sunlight becoming Dark reddish brown [44. d.rBr] with age.

*Glands.*—Number: 1 to 3. Position: Alternate, the first 2 are positioned on the petiole and the third one is at the intersection of the petiole and blade. Size: Small. Form: Globose. Color: Strong yellow green [117. s.YG] becoming Dark reddish brown [44. d.rBr] with age.

*Leaf buds.*—Small, pointed to conic, Dark grayish reddish brown [47. d.gy.rBr] in color.

Flower buds:

*Hardiness.*—Hardy, with respect to central California winters.

*Diameter.*—Typically 3/16" [4.8 mm.] 3 days before bloom.

*Length.*—Typically ⅜" [9.5 mm.] 3 days before bloom.

*Form.*—Not appressed.

*Surface.*—Pubescent.

*Color.*—White [263. White] with a Light purplish pink [249. l.pPk] tip.

Flowers: Perfect, complete, perigynous, usually a single pistil, typically twenty-four or more stamens, five sepals and petal locations alternately positioned.

*Average flower diameter.*—⅞" [22.2 mm.].

*Number of pistils.*—Usually five, rarely more.

*Petal shape.*—Circular.

*Petal margin.*—Somewhat wavy.

*Average petal diameter.*—⅜" [9.5 mm.].

*Average petal length.*—⅜" [9.5 mm.].

*Petal apex.*—Rounded, some emarginate.

*Petal base.*—Rounded.

*Petal color.*—White [263. White] with a Light purplish pink [249. l.pPk] margin on some.

*Anther color.*—Moderate purplish pink [250. m.pPk] over a Pale yellow [89. p.Y] center.

*Stigma color.*—Light greenish yellow [101. l.gY].

*Sepal color.*—Dark purplish red [259. d.pR] with Moderate greenish yellow [102. m.gY] centers on some.

*Sepal length.*—5/32" [4.0 mm.].

*Sepal width.*—⅛" [3.2 mm.].

*Average pistil length.*—½" [12.7 mm.].

*Average stamen length.*—⅜" [9.5 mm.].

*Fragrance.*—Moderate.

*Pollen production.*—Abundant.

*Blooming period.*—Very late compared to apricots, late compared to plums, about one week later than 'Santa Rosa' (unpatented) plum.

*Onset of bloom.*—One percent on Mar. 1, 2003.

*Date of full bloom.*—Mar. 9, 2003.

*Duration on bloom.*—One to two weeks, dependent on ambient temperature.

*Number per cluster.*—Average 5, up to 12 observed.

Fruit

Maturity when described: Firm to ripe, Jun. 28, 2003.

Date of first picking: Jun. 22, 2003.

Date of last picking: Jul. 1, 2003.

Size: Uniform, medium compared to apricots.

*Average diameter axially.*—2⅛" [54.0 mm.].

*Average diameter across suture plane.*—2¼" [57.2 mm.].

*Typical weight.*—3.6 ounces [102 grams].

Form:

*Longitudinal section form.*—Round to slightly oblate on some.

*Transverse section through diameter.*—Round.

Suture: An inconspicuous line becoming a very shallow groove toward the apex.

Ventral surface: Rounded.
Lips: Slight to none.
Cavity: Flaring, circular with suture not showing.
*Depth.*—5/16" [7.9 mm.].
*Breadth.*—3/4" [19.1 mm.].
Base: Slightly truncate.
Apex: Rounded.
Pistil point: A slightly depressed inconspicuous Light yellowish brown [76. l.yBr] dot.
Stem: Medium.
*Average length.*—3/8" [9.5 mm.].
*Average width.*—3/32" [2.4 mm.].
Skin:
*Thickness.*—Medium.
*Surface.*—Smooth.
*Tenacity.*—Tenacious to flesh.
*Astrigency.*—Very slightly astringent.
*Tendency to crack.*—None observed.
*Color.*—Blackish red [21. blackish R] to a Very dark red [17. v.d.R] with very slight Light yellowish brown [76. 1.yBr] freckling.
*Surface bloom.*—Absent.
*Pubescence.*—Moderate, does not roll up when rubbed, similar to an apricot.
Flesh:
*Color.*—Strong orange yellow [68. s.OY] toward the stone, Strong yellow [84. s.Y] toward the skin.
*Surface of pit cavity.*—Deep orange yellow [69. deep OY] fibers broken when twisted from stone.
*Amygdalin.*—Scarce.
*Juice.*—Moderate, very rich.
*Texture.*—Very firm, crisp.
*Fibers.*—Very abundant, fine.
*Ripens.*—Quite evenly.
*Flavor.*—Very sweet with moderate to low acid, typically having brix levels ranging from 20 to 24.
*Aroma.*—Slight.
*Eating quality.*—Outstanding with no bitter skin.

Stone

Type: Clingstone.
Form: Oval.
Hilum: Very narrow.
Base: Straight.
Apex: Rounded to cuneate with an average angle of 135 degrees.
Sides: Equal.
Surface: Rough, like an apricot.
External color of stone: Light brown [57. l.Br].
Cavity surface color: Dark yellowish brown [78. d.yBr].
Average pit wall thickness: 1/16" [1.6 mm.].
Average width: 11/16" [17.5 mm.].
Average length: 1" [25.4 mm.].
Average breadth: 3/8" [9.5 mm.].
Tendency to split: None observed.
Kernel:
*Form.*—Oval.
*Pellicle color.*—Grayish yellowish brown [80. gy.yBr].
*Skin color.*—Pale orange yellow [73. p.OY] becoming Moderate orange yellow [71. m.OY] at the apex.
*Taste.*—Very bitter.
*Viable.*—Yes.
*Average width.*—7/16" [11.1 mm.].
*Average length.*—5/8" [15.9 mm.].
*Amygdalin.*—Abundant.

Use

Market: Fresh market and long distance shipping.
Keeping quality: Good. Fruit quality observed to remain in good condition after 14 days in standard cold room at 36° Fahrenheit [2° Calsius].
Shipping quality: Excellent.
Resistance to insects: No unusual susceptibilities noted.
Resistance to diseases: No unusual susceptibilities noted.

Other Notes

Although the new variety of interspecific tree possesses the described characteristics under the ecological conditions at Le Grand, Calif., in the central part of the San Joaquin Valley, it is to be expected that variations in these characteristics may occur when farmed in areas with different climatic conditions, different soil types, and/or varying cultural practices.

I claim:

1. A new and distinct variety of interspecific tree, substantially as illustrated and described, that is similar to its seed parent, 'Angeleno' (U.S. Plant Pat. No. 2,747) plum, by being self-unfruitful and by producing fruit that is globose in shape, firm in texture, and dark purple in skin color, but is distinguished therefrom by having apricot type leaves and blossoms and by producing fruit that has pubescent skin, that is orange yellow in flesh color, that is much sweeter in flavor, and that matures in late June rather than early September, or about twenty days earlier.

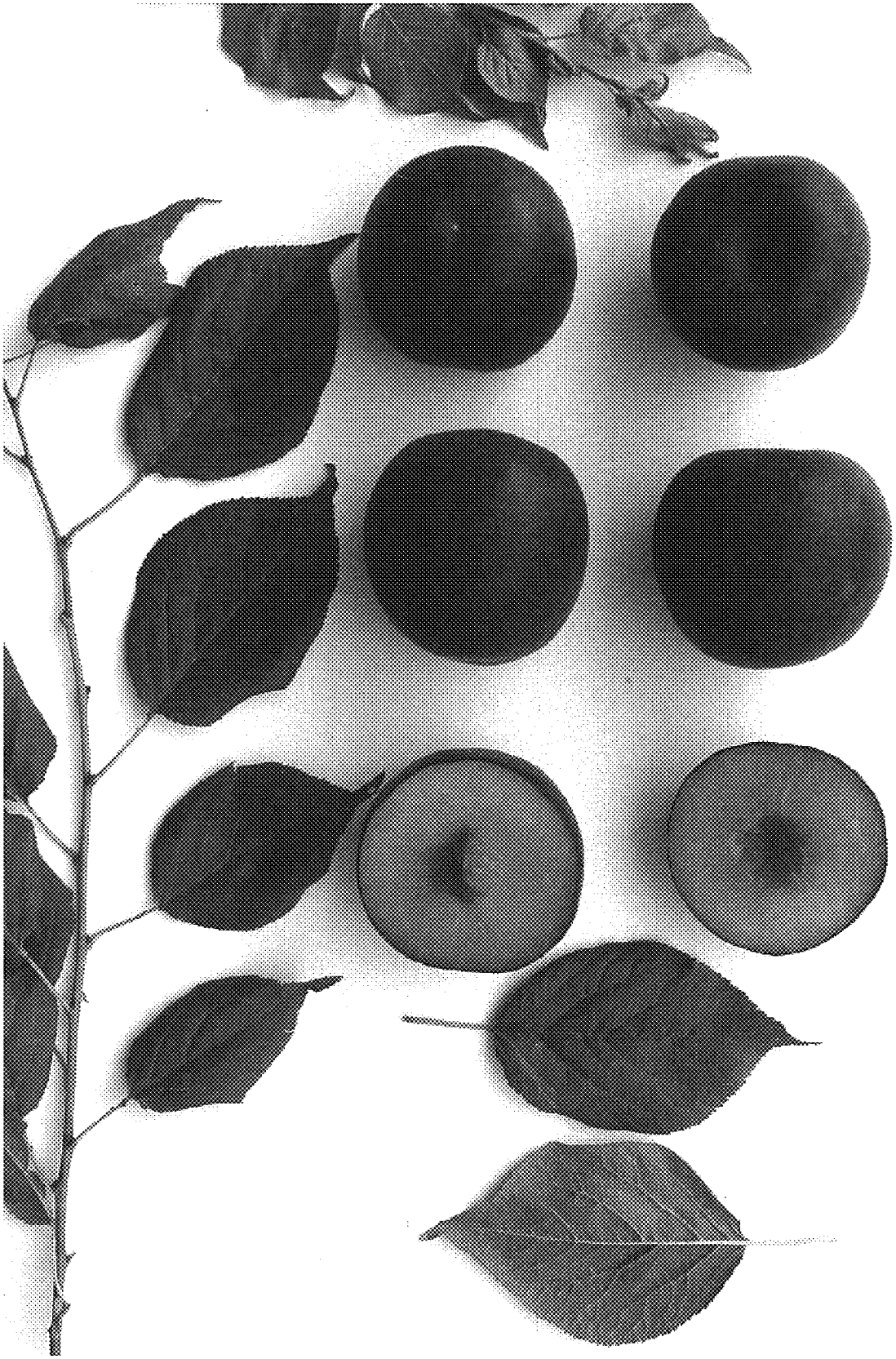

* * * * *